(12) United States Patent
Hillebrand

(10) Patent No.: US 10,131,935 B2
(45) Date of Patent: Nov. 20, 2018

(54) METHOD FOR PARALLEL ISOLATION OF VIRAL NUCLEIC ACIDS

(75) Inventor: Timo Hillebrand, Hoenow (DE)

(73) Assignee: AJ INNUSCREEN GmbH, Berlin (DE)

(*) Notice: Subject to any disclaimer, the term of this patent is extended or adjusted under 35 U.S.C. 154(b) by 214 days.

(21) Appl. No.: 12/352,170

(22) Filed: Jan. 12, 2009

(65) Prior Publication Data
US 2009/0253903 A1    Oct. 8, 2009

(30) Foreign Application Priority Data
Jul. 11, 2006  (DE) .................. 10 2006 032 610

(51) Int. Cl.
C12Q 1/70       (2006.01)
C12Q 1/6806   (2018.01)

(52) U.S. Cl.
CPC .......... *C12Q 1/6806* (2013.01); *C12Q 1/701* (2013.01)

(58) Field of Classification Search
None
See application file for complete search history.

(56) References Cited

U.S. PATENT DOCUMENTS

| | | | |
|---|---|---|---|
| 5,808,041 A * | 9/1998 | Padhye et al. | 536/25.4 |
| 6,180,778 B1 * | 1/2001 | Bastian et al. | 536/25.4 |
| 6,383,393 B1 * | 5/2002 | Colgan et al. | 210/656 |
| 6,936,414 B2 * | 8/2005 | Gundling | 435/6.12 |
| 2005/0032105 A1 * | 2/2005 | Bair et al. | 435/6 |
| 2005/0214926 A1 * | 9/2005 | Zielenski et al. | 435/270 |
| 2005/0239068 A1 * | 10/2005 | Bosnes | 435/6 |
| 2006/0281092 A1 * | 12/2006 | Wille et al. | 435/6 |
| 2009/0234112 A1 * | 9/2009 | Hillebrand | 536/55.3 |

FOREIGN PATENT DOCUMENTS

| | | |
|---|---|---|
| DE | 198 56 064 | 6/2000 |
| DE | 102 53 351 | 5/2004 |
| EP | 389063 A2 * | 9/1990 |
| EP | 1 524 317 | 4/2005 |
| WO | WO 96/18731 | 6/1996 |
| WO | WO 99/40098 | 8/1999 |
| WO | WO 03/046213 | 6/2003 |
| WO | WO 2004/055207 | 7/2004 |
| WO | WO 2005010209 A2 * | 2/2005 |

OTHER PUBLICATIONS

Bavykin et al. Applied and Environmental Microbiology (2001) 67: 922-928.*
Candotti et al. Journal of Virological Methods (2004) 118: 39-47.*
U.S. Appl. No. 12/349,095, filed Jan. 6, 2009, Hillebrand.
Michael K. Hourfar, et al., "High-Througput Purification of Viral RNA RNA Based on Novel Aqueous Chemistry for Nucleic Acid Isolation", Clinical Chemistry 51:7, 1217-1222 (2005).
R. Boom, et al., "Rapid and Simple Method for Purification of Nucleic Acids", Journal of Clinical Microbiology, Mar. 1990, pp. 495-503.
U.S. Appl. No. 12/857,299, filed Aug. 16, 2010, Hillebrand, et al.

* cited by examiner

*Primary Examiner* — Angela M. Bertagna
(74) *Attorney, Agent, or Firm* — Grüneberg and Myers PLLC

(57) ABSTRACT

Parallel isolation of a double-stranded nucleic acid and a single-stranded nucleic acid is possible from a sample that contains these acids, without separating the acids, by mixing the sample with a lysis buffer having high salt concentration or low salt concentration, or having a proteolytic enzyme. The sample that contains nucleic acid before its lysis, or the sample that has already been lysed or homogenized, is adjusted with a binding buffer in such a manner that the total nucleic acid is adsorbed onto a solid carrier. The binding buffer contains at least one non-ionic detergent in a high concentration. With the exception of the detergent, the sample contains no other non-acidic organic component miscible in water. The carrier with the adsorbed total nucleic acid is removed. The adsorbed total nucleic acid is washed and eluted.

12 Claims, No Drawings

METHOD FOR PARALLEL ISOLATION OF VIRAL NUCLEIC ACIDS

BACKGROUND OF THE INVENTION

Field of the Invention

The invention relates to a method for fast, simple, and highly sensitive isolation of viral nucleic acids.

Description of the Related Art

The examination of diagnostically relevant biological samples (serum, plasma, blood, spinal fluid, swab samples, abraded organ tissue, etc.) for the detection of infectious pathogens is increasingly gaining importance. Virus infections such as HIV, HCV, or HBV are continuing to spread more strongly worldwide. Furthermore, the massive occurrence of new types of virus diseases (e.g. bird flu) requires a fast and flexible reaction for sensitive diagnostic virus detection. New test methods on the basis of using sensitive amplification techniques such as Real Time PCR allow highly efficient virus detection, and are increasingly being used as diagnostic instruments. The step of molecular sample preparation in the form of isolation of the nucleic acids to be detected is increasingly gaining importance.

The sensitivity of the test system is decisively influenced by the process of isolation of the nucleic acid.

A number of extraction methods exist, which allow isolation of viral nucleic acids. U.S. Pat. No. 5,234,809 describes a process for isolation of nucleic acids from starting materials that contain nucleic acid, by means of incubation of the starting material with a chaotropic buffer and a solid phase that binds DNA. The solid phase consists of silicate mineral particles which are >50 nm. The chaotropic buffers implement both lysis of the starting material and binding of the nucleic acids to the solid phase. The method is well suited for isolating nucleic acids from small sample amounts, and finds its practical use particularly in the sector of the isolation of viral nucleic acids. However, it has been shown in practical use that the method described in U.S. Pat. No. 5,234,809 brings with it a number of disadvantages. The use of particulate systems for binding of the nucleic acids to be isolated is fundamentally very complicated in its handling. Furthermore, it has been shown that the use of buffers on the basis of the use of chaotropic salts is often not sufficient with regard to a required, highly sensitive virus detection.

Other methods describe chromatographic purification and separation of nucleic acids from a solution that has a high salt concentration and a high alcohol concentration.

The solution is again brought into contact with a carrier material for binding the nucleic acids. Subsequently, the carrier material is washed with known alcoholic washing buffers, and the bound nucleic acid is finally dissolved from the carrier material again, by means of water or a low-salt buffer.

The method implements efficient isolation and, if necessary, also separation of nucleic acids/nucleic acid mixtures, and is simple and quick in its implementation. The improvement as compared with U.S. Pat. No. 5,234,809 is achieved by means of the addition of an alcohol to the initial lysis buffer. This step allows an improvement in efficiency of the extraction process, which makes it possible to isolate even nucleic acid targets from a clinical sample, in sensitive manner.

Another method for separation and isolation of single-stranded and double-stranded nucleic acids is disclosed in EP 1 146 049 A2. The method is based on the treatment of a source that contains nucleic acids, using at least one mineral carrier material, in such a form that:

1. the single-stranded nucleic acid is isolated, in that the treatment conditions are adjusted by means of an aqueous mixture of chaotropic salts and low aliphatic alcohols, in such a manner that subsequently, the single-stranded nucleic acid is primarily adsorbed onto a mineral carrier, while the double-stranded nucleic acid is not adsorbed. The bound, single-stranded nucleic acid is subsequently washed and finally eluted from the carrier material by means of a low-salt buffer.
2. the double-stranded nucleic acid is isolated, in that the treatment conditions are adjusted by means of a mixture of substances that complex earth-alkali ions, without low aliphatic alcohols, in such a manner that subsequently, the double-stranded nucleic acid is primarily adsorbed onto a mineral carrier, while the single-stranded nucleic acid is not adsorbed. The bound, double-stranded nucleic acid is subsequently washed and finally eluted from the carrier material by means of a low-salt buffer.
3. the double-stranded nucleic acid is isolated in that the treatment conditions are adjusted by means of the presence of a sarcosinate but without low aliphatic alcohols, in such a manner that subsequently, the double-stranded nucleic acid is primarily adsorbed onto a mineral carrier, while the single-stranded nucleic acid is not adsorbed. The bound, double-stranded nucleic acid is subsequently washed and finally eluted from the carrier material by means of a low-salt buffer.
4. the double-stranded or single-stranded nucleic acid is isolated in that the treatment conditions are adjusted by means of an aqueous mixture of chaotropic salts and low aliphatic alcohols, in such a manner that both nucleic acid fractions adsorb onto a mineral carrier. Separation of the nucleic acids takes place by means of selective elution. In this connection, the double-stranded nucleic acid is dissolved from the carrier material by means of a solution having a reduced ion strength and low aliphatic alcohols. The remaining single-stranded nucleic acid is subsequently washed and finally dissolved from the carrier material by means of a low-salt buffer.

Alternatively to this, the single-stranded nucleic acid can be selectively eluted from the carrier material by means of a solution that contains substances that complex earth-alkali ions and/or contains sarcosinates. The now remaining double-stranded nucleic acid is subsequently washed, once again, and finally dissolved from the carrier material by means of a low-salt buffer.

Again, the method is simple in its implementation, and can isolate DNA or RNA from biological samples. Although EP 1 146 049 A2 relates to the separation of nucleic acid mixtures, it becomes clear to a person skilled in the art, when reading, for example, dependent claim 4, that again, as described above, binding of nucleic acids to a mineral material is implemented by means of the combination of a salt solution with an alcohol. Again, the decisive factor for the step of binding of nucleic acids to mineral materials, in this connection, is the existence of an alcohol in the buffers used for the extraction process. Thus, the background art indicates that isolation of nucleic acids from biological samples using chaotropic salts alone works, but that the method only becomes really efficient by adding an alcohol (i.e. a combination of a solution that contains salt with an aliphatic alcohol).

In the European patent application EP 1 524 317 A1, a lysis buffer is described, among other things, that contains 5% Triton and no indication of an alcohol. In Example 1, a buffer is used that is composed of 6 M guanidine hydrochloride, 10 mM tris-HCl, and 20% Triton X-100. This buffer is added to the biological sample. Afterwards, the addition of proteinase K also takes place. Subsequently, incubation at 70° C. takes place. It is obvious that this buffer, in combination with the proteinase K, thus fulfills the function of a lysis buffer. After the lysis, another component is added to the batch (e.g. isopropanol, acetonitrile, DMSO, or methyl ethyl ketone), whereby this involves a non-acidic organic component miscible in water. In another example, N-methyl-2-pyrrolidone, or, alternatively to this, isopropanol is also used as a "non-acidic" organic component. As Example 3 explains, this also relates to the isolation of DNA by means of binding of the nucleic acid to magnetic particles. Here, too, the addition of N-methyl-2-pyrrolidone shows similar yields as the addition of isopropanol. Example 4 also uses a lysis buffer, whereby again, after lysis of the sample, the addition of a binding conditioner (gamma butyl lactone, propylene carbonate, or again, N-methyl-2-pyrrolidone) takes place. The detergent component that is listed in EP 1 524 317 A1 (Triton X-100) is merely a component of the lysis buffer. However, there is no indication at all that this component mediates binding of DNA or RNA. According to the patent specification, this is implemented by means of the additional addition of the non-acidic organic components according to the invention. It turns out that the lysis buffer is not able to implement isolation of nucleic acids. For the isolation of DNA or RNA, the listed organic acid must be added. The components listed in EP 1 524 317 A1 are furthermore also highly toxic (e.g. DMSO) and represent a significant hazard potential.

DETAILED DESCRIPTION OF THE INVENTION

The present invention was based on the object of eliminating the disadvantages that have become known in the background art.

It was possible to accomplish this and other objects according to the invention in surprisingly simple manner.

In one embodiment, the present invention provides a method for parallel isolation of a double-stranded nucleic acid and a single-stranded nucleic acid from a sample that contains said double-stranded nucleic acid and said single-stranded nucleic acid, without separating the double-stranded and single-stranded nucleic acids, comprising:

mixing said sample with a lysis buffer having high salt concentration or low salt concentration, or having a proteolytic enzyme,
wherein
  a) the sample that comprises nucleic acid before its lysis, or the sample that has already been lysed or homogenized, is adjusted with a binding buffer in such a manner that the total nucleic acid is adsorbed onto a solid carrier,
  the binding buffer comprises at least one non-ionic detergent in a high concentration, and,
  with the exception of the detergent, the binding buffer comprises no other non-acidic organic component miscible in water,
  b) the carrier with the adsorbed total nucleic acid is removed,
  c) the adsorbed total nucleic acid is washed and eluted.

In one embodiment, the sample is mixed with a lysis buffer having high salt concentration (preferably about above 4M) or low salt concentration (preferably about below 4M) and/or having a proteolytic enzyme.

In the context of the present invention, the following abbreviations have the following meaning: SDS-sodium dodecyl sulfate, LDS-lithium dodecyl sulfate, EDTA-ethylenediaminetetraacetic acid and EGTA-ethylene glycol tetraacetic acid.

According to the invention, an alternative method was made available, which makes it possible to isolate nucleic acids from a sample that contains nucleic acids, in a fast, simple, and inexpensive manner, whereby the solutions required for selective binding of the nucleic acids—with the exception of detergents—do not contain any non-acidic organic components miscible with water, such as alcohol, acetonitrile, DMSO, or methyl ethyl ketone, for example. In this connection, the method makes it possible to isolate DNA (double-stranded nucleic acid) and RNA (single-stranded nucleic acid) from a starting sample at the same time, and thus without bringing about any separation of nucleic acid mixtures. In particular, the method is able to isolate highly sensitive viral nucleic acids from diagnostically relevant biological samples.

In this connection, it should be noted that EDTA and sodium citrate, for example, as salts of organic acids, are not included among the non-acidic organic components miscible in water.

Surprisingly, highly efficient isolation of nucleic acids from a biological sample can also be achieved in a completely different way than described in the background art, without using alcohol as a component, which was essential for this up to now.

The method according to the invention is based on lysis of a biological sample with known lysis buffers. The lysis buffers contain known chaotropic salts having a high ion intensity, or combinations of chaotropic salts having a high ion intensity with a sarcosinate and other additives, if necessary. These buffer systems, in their known function, allow the digestion and denaturing of a biological sample, and also bring about inactivation of endogenic RNases. This is particularly important with regard to the isolation of RNA. Also, lysis buffers that represent a combination of chaotropic salts and other salts, and that also contain detergents, if necessary, and other additives, if necessary, to support the lysis process, can be used, whereby in the case of the chaotropic salts, no known high ion intensities are required. Such a combination then allows efficient inclusion of proteolytic enzymes (e.g. proteinase K) for effective digestion of the starting material.

After lysis of the starting material, the binding conditions for binding of the nucleic acids contained in the sample to a mineral carrier material are then adjusted.

This takes place, in the method according to the invention, not by means of adding an alcohol, but surprisingly, by means of adding a non-ionic detergent, such as Tween-20, Tween-80, or Triton X-100, for example, in a high concentration. In one embodiment, the addition of the detergent is a preferred step. Adjustment of an acidic pH value is advantageous. According to the invention, the detergent completely replaces the function of adding an alcoholic component, which was necessary for this up to now. The lysis batch that is mixed with the detergent is subsequently brought into contact with a carrier, preferably a mineral carrier or surface-functionalized magnetic particles or iron oxide particles, thereby causing the nucleic acids to be isolated to adsorb onto the mineral carrier. The mineral carrier is subsequently washed with known washing buffers and finally dissolved from the mineral material, again by means of water or a low-salt buffer. The detergent component that is required for binding of the nucleic acids can furthermore also be present as a mixture of detergent with other salts and other additives, if necessary. In this way, optimal binding conditions can be achieved in the combination of salt/detergent, in each instance, without this having any influence on the initial use of an efficient lysis buffer. For example, a lysis buffer that has only a low salt concentration (which would not be sufficient to mediate efficient binding of the nucleic acids to be isolated, in combination with a detergent) can be used for the initial sample digestion. After sample digestion, a binding buffer that has a non-ionic detergent in high concentration and, in addition, a high salt concentration, is then added to the reaction batch. In this way, the binding conditions that efficiently mediate quantitative isolation of the viral nucleic acids are then adjusted. The deciding factor is preferably that by way of the binding buffer on the basis of a high concentration of non-ionic detergents, the other components that allow efficient binding of the nucleic acids to be isolated are also made available. A binding buffer containing at least one non-ionic detergent comprising a salt solution having a high concentration of greater than 1 M, and a lysis buffer having a low salt concentration of less than 100 mM may be used.

The method is therefore completely alternative to the methods described that require an alcohol or other substances such as acetonitrile, DMSO, or methyl ethyl ketone for efficient binding of nucleic acids to mineral carrier material. Furthermore, it allows parallel isolation of double-stranded and single-stranded nucleic acids from a biological sample, without separating the double-stranded and single-stranded nucleic acids. Furthermore, a decisive advantage also consists in the fact that great flexibility with regard to the selection of the lysis buffer is achieved. In this way, known, efficiently acting lysis buffers, including proteolytic enzymes, can also be used. Adjustment of the binding conditions for nucleic acids for their adsorption onto a mineral carrier material always takes place after lysis of the starting material, by means of the addition of the binding buffer according to the invention, containing a high concentration of a non-ionic detergent and containing other additives, if necessary.

The invention makes parallel isolation of double-stranded and single-stranded nucleic acids from a sample that contains nucleic acids possible, for the first time, whereby the sample that contains nucleic acids is incubated with a buffer that consists either of a salt solution of chaotropic salts, or a salt solution of chaotropic salts having a low ion intensity (less than 100 mM, preferably less than 50 mM) and other non-chaotropic salts, and, if necessary, other additives such as detergents (SDS, sarcosinate, LDS), proteolytic enzymes, complex-forming compounds (EDTA, EGTA); digestion of the biological sample takes place under these conditions, so that the nucleic acids are released into the buffer.

According to the invention, by means of the addition of a binding buffer comprising:
  a) a non-ionic detergent, or
  b) a mixture of a non-ionic detergent with water, or
  c) a mixture of a non-ionic detergent with a salt solution
    and, if necessary, other additives, but without other non-acidic organic components miscible in water, such as alcohol, conditions are adjusted that make it possible to adsorb both double-stranded and single-stranded nucleic acids to a mineral material (carrier). The concentration of detergent for binding of the nucleic acids amounts to 5-50 wt. %; preferably 10-30 wt. % in the final mixture of lysis buffer/binding buffer. The concentration of detergent for binding of the nucleic acids includes all values and subvalues therebetween, especially including 10, 15, 20, 25, 30, 35, 40 and 45 wt. %.

The mineral material subsequently washed with washing buffer and the nucleic acids dissolved from the mineral material again by means of water or low-salt buffer.

Another object of the invention is a kit for carrying out the method according to the invention.

The use according to the invention consists in the fact that non-ionic detergents are used in a concentration of 5-50 wt. %; preferably 10-30 wt. %, in the absence of alcohol, for parallel isolation of single-stranded and double-stranded nucleic acids, from samples containing these substances, without separating the double-stranded and single-stranded nucleic acids, by means of binding the total nucleic acids to a solid carrier. The invention is particularly advantageous in the isolation of viral nucleic acids.

Having generally described this invention, a further understanding can be obtained by reference to certain specific examples which are provided herein for purposes of illustration only, and are not intended to be limiting unless otherwise specified.

EXAMPLES

Two blood plasma samples were spiked with HIV viruses and HBV viruses, and used for isolation of the viral nucleic acid. 150 µl of the sample were transferred to a 1.5 ml reaction vessel. The sample was subsequently mixed with 450 µl of a lysis buffer (4 M guanidine thiocyanate, 80 mM tri-sodium citrate dehydrate) and vortexed for 10 s. Subsequently, the sample was incubated at room temperature for 10 min. After lysis and denaturing of the starting sample, 600 µl of a binding buffer (30% Tween-20, 5 mM EDTA, 20 mM tri-sodium citrate dehydrate) were added, and the sample was mixed thoroughly. It is advantageous to adjust the binding buffer to an acidic pH, for example using an acetate buffer. The batch was subsequently centrifuged over a filter column that contained a commercially available glass fiber filter paper (Whatmann company). The filter column was subsequently washed with alcoholic washing buffers. Elution of the bound viral nucleic acid took place by adding 50 µl RNAse-free water.

The isolated nucleic acid was then analyzed for specific virus detection of HIV and HBV, by means of real-time PCR. Detection of the viral nucleic acids was successful. Results:

| Plasma sample | Virus detection | CT Value |
|---|---|---|
| Sample 1 | HIV 1000 IU/ml | 34.33 |
| Sample 2 | HBV 500 IU/ml | 30.52 |
| Sample 3 | HIV 1000 IU/ml | 34.86 |
| Sample 4 | HBV 500 IU/ml | 30.78 |

German patent application DE 10 2006 032 610.5 filed Jul. 11, 2006, and PCT/EP2007/057131, filed Jul. 11, 2007, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method for parallel isolation of a viral double-stranded nucleic acid and a viral single-stranded nucleic acid from a sample that comprises said double-stranded nucleic acid and said single-stranded nucleic acid, without separating the double-stranded and single-stranded nucleic acids, the method comprising:
   (a) mixing said sample with a lysis buffer comprising less than 100 mM of a chaotropic salt and at least one non-chaotropic salt, and, optionally, including a proteolytic enzyme,
   (b) adjusting the sample, that comprises viral nucleic acid before its lysis or the sample that has already been lysed with the lysis buffer, with a binding buffer, in the absence of alcohol, in such a manner that the total nucleic acid is adsorbed onto a solid carrier,
   wherein the binding buffer comprises a high concentration of at least one non-ionic detergent, and the detergent concentration for binding the nucleic acids is from 5 to 50 wt. % in the final mixture of the lysis buffer and the binding buffer, wherein the lysis buffer and the binding buffer facilitate adsorption of the total nucleic acid onto the solid carrier,
   wherein the lysis buffer has a salt concentration of 100 mM or less and the binding buffer containing at least one non-ionic detergent comprises a salt at a concentration of greater than 1 M, and
   wherein the binding buffer does not contain any non-acidic organic component miscible with water, with the exception of the at least one non-ionic detergent,
   (c) removing the solid carrier with the adsorbed total nucleic acid, and
   (d) washing and eluting the adsorbed total nucleic acid.

2. The method according to claim 1, wherein the binding buffer is adjusted to an acidic pH value.

3. The method according to claim 1, wherein the detergent concentration for binding the nucleic acids is from 10 to 30 wt. % in the final mixture of the lysis buffer and the binding buffer.

4. The method according to claim 1, wherein the binding buffer further comprises
   a) SDS, sarcosinate, LDS, and/or
   b) a chelating agent.

5. The method according to claim 1, wherein a mineral carrier or magnetic iron oxide particles are used as the solid carrier.

6. The method according to claim 1, wherein the solid carrier is a component of a mini-centrifugation column.

7. The method according to claim 1, wherein the binding buffer comprises EDTA, sodium citrate or a mixture thereof.

8. The method according to claim 1, wherein the binding buffer further comprises EDTA or EGTA.

9. The method according to claim 1, wherein a mineral carrier or magnetic iron oxide particles having modified surfaces are used as the solid carrier.

10. The method according to claim 1, wherein the adjusting (b) with the binding buffer is conducted when the sample has already been lysed with the lysis buffer.

11. The method according to claim 1, wherein the concentration of the non-ionic detergent in the binding buffer is 30% or greater.

12. The method according to claim 1, wherein said double-stranded nucleic acid comprises DNA and said single-stranded nucleic acid comprises RNA.

* * * * *